US006181967B1

(12) United States Patent
Alt

(10) Patent No.: US 6,181,967 B1
(45) Date of Patent: Jan. 30, 2001

(54) ATRIAL DEFIBRILLATOR APPARATUS AND METHOD OF USE

(76) Inventor: Eckhard Alt, Eichendorffstrasse 52, Ottobrunn (DE), 85521

( * ) Notice: Under 35 U.S.C. 154(b), the term of this patent shall be extended for 0 days.

(21) Appl. No.: 09/361,406

(22) Filed: Jul. 27, 1999

Related U.S. Application Data

(63) Continuation-in-part of application No. 08/906,352, filed on Aug. 5, 1997, now Pat. No. 5,928,269, which is a continuation-in-part of application No. 08/630,907, filed on Apr. 4, 1996, now Pat. No. 5,653,734, which is a continuation of application No. 08/222,242, filed on Apr. 4, 1994, now Pat. No. 5,571,159.

(51) Int. Cl.$^7$ ..................................................... A61N 1/39
(52) U.S. Cl. ................................................................ 607/5
(58) Field of Search ............................................ 607/5, 126

(56) References Cited

U.S. PATENT DOCUMENTS

| 3,952,750 | * | 4/1976 | Mirowski et al. | 607/5 |
| 5,578,063 | * | 11/1996 | Bocek et al. | 607/5 |
| 5,827,326 | * | 10/1998 | Kroll et al. | 607/5 |

* cited by examiner

Primary Examiner—William E. Kamm
(74) Attorney, Agent, or Firm—Blank Rome Comisky & McCauley LLP

(57) ABSTRACT

A method for external treatment of dysrhythmias including fibrillation of a patient's heart utilizes an externally located control box which generates electrical waveforms including shocks of variable energy content sufficient for terminating the dysrhythmias. A lead having transvenous defibrillation electrodes is inserted through a portion of the patient's venous system to position the electrodes to produce an electric field vector through the patient's heart when an electrical shock of sufficient energy content is applied across the electrodes. The control box is electrically connected to the lead to deliver electrical shocks from the control box to the electrodes, and to deliver a representation of the patient's ECG waveform to the control box. A display screen on the control box aids in synchronously triggering the electrical shocks in response to detection of the QRS complex of the ECG waveform. The energy content of each electrical shock is adjusted from the control box to a value within a range from one to thirty joules, to terminate a detected event of fibrillation.

9 Claims, 3 Drawing Sheets

ATRIAL DEFIBRILLATOR APPARATUS AND METHOD OF USE

CROSS REFERENCE TO RELATED APPLICATIONS

This application is a continuation-in-part of application Ser. No. 08/906,352, filed Aug. 5, 1997, now U.S. Pat. No. 5,928,269, issued Jul. 27, 1999, which is a continuation-in-part of Ser. No. 08/630,907, filed Apr. 4, 1996, now U.S. Pat. No. 5,653,734, which is a continuation of Ser. No. 08/222,242, filed Apr. 4, 1994, now U.S. Pat. No. 5,571,159, each of which is in the name of the applicant herein, and for which priority is claimed as to common subject matter.

BACKGROUND OF THE INVENTION

The present invention relates generally to treatment of fibrillation by discharge of electrical energy in the region of the heart for converting the dysrhythmia to sinus rhythm, and more particularly to monitoring and treatment of rhythm disorders, primarily atrial but also ventricular, using an external defibrillator in conjunction with a temporary or permanent implanted catheter.

Greater human longevity has resulted in significant increases in the number of cases of atrial fibrillation, and to an extent ventricular fibrillation, particularly in the industrial nations. Atrial fibrillation is one of the primary causes of hospitalization for cardiac rhythm disorders in the United States, and an underlying cause of events of cerebrovascular stroke. Proper and timely treatment and cardioversion of atrial fibrillation would noticeably enhance expectancy and quality of life, and reduce hemodynamic and thromboembolic complications. Anti-arrhythmic drugs have not been effective to measurably reduce the incidence of atrial fibrillation, and have undesirable side effects.

Application of external shocks with energies of between 100 and 350 joules is one therapy for treating atrial fibrillation, but it, too, has a number of risks and complications. Among them are late ventricular fibrillation, pericarditis attributable to the high electrical current, and spinal and other skeletal fractures arising from severe muscular contractions during application of the high energy shock(s).

The art of implanted atrial defibrillation electrodes using lower energies is well developed, as indicated for example by the disclosure of U.S. Pat. No. 5,282,837 to J. Adams et al. The '837 patent describes the discharge of defibrillating energy from an implanted defibrillator, between two electrodes of an implanted catheter threaded through the coronary sinus. Energy discharge electrodes of the catheter are positioned beneath the left atrium near the left ventricle and in a region adjacent the right atrium coronary sinus ostium to minimize the potential for ventricular fibrillation. The implanted defibrillator senses arrhythmia and controls the energy discharge.

Ventricular fibrillation is also arrested with implanted systems as disclosed by Shulte et al in U.S. Pat. No. 5,269,319. In the '319 patent disclosure, two defibrillation electrodes on a single catheter are inserted via the superior vena cava into the right atrium and right ventricular cavity respectively. R-waves are detected and defibrillation impulse energy is synchronized therewith.

It is a principal aim of the present invention to provide improved treatment of atrial fibrillation, and to an extent, ventricular fibrillation.

Another aim of the invention is to significantly reduce the amount of energy required for treatment of atrial fibrillation from external impulse generators, by means of a hybrid system of internal defibrillating electrodes powered by external energy and control means.

Additional problems exist with implanting prior art electrodes and delivery of sufficient energy for defibrillation. Permanently implanted systems are of questionable value if only used for treating atrial fibrillation. In general, effective electrodes employed in the past have required large electrode surface areas to handle high energy impulses, and are thus substantially intrusive. Implantation of netting, barbs and other forms of electrodes or electrode anchoring on or in the vicinity of the heart has also presented a number of problems, and have not been entirely feasible for use with a temporary defibrillation system.

Conditions such as the potential for congestive heart failure can require continuous monitoring after defibrillation rather than or in addition to mere isolated shock treatment. Furthermore, cardiac surgery may call for post-operative monitoring for atrial dysrhythmias, and the delivery of instantaneous treatment when atrial fibrillation is detected.

Accordingly, it is a further object of the invention to provide a method and associated instrumentation for relatively brief periods during hospitalization or clinical study, for example, of continuous monitoring and instantaneous treatment of dysrhythmias, particularly atrial fibrillation, with moderate energy shocks of adequate electrical field gradient to defibrillate when necessary, and with a need only to implant a catheter or lead for delivery of electrical energy to the appropriate region(s) of the heart.

SUMMARY OF THE INVENTION

The present invention provides improvements in monitoring and treatment of dysrhythmias such as atrial fibrillation, using methods and apparatus which reduce risk of complications encountered with prior art techniques, and which allow effective treatment of dysrhythmias, and reduced risk of congestive heart failure and post-operative cardiac surgery problems, with relatively little delay. Treatment is generally required only for brief periods during hospitalization or clinical monitoring and evaluation of the patient.

The aforementioned related '734 patent discloses a method of treating atrial fibrillation in which a temporary catheter is inserted into the patient's body, the catheter having a thin elongate flexible body with spaced-apart low impedance defibrillation electrodes that conform in shape to the catheter body to maintain a smooth continuous surface therewith. An inflatable balloon at the distal end is used to anchor the catheter. The distal end of the catheter body is advanced through the superior vena cava along a path including right atrium, right ventricle and pulmonary artery adjacent the left atrium, until the more distal electrode is positioned in the pulmonary artery adjacent the left atrium and the other electrode is located in the right atrium. Selective inflation of the balloon aids maneuvering of the catheter as it is advanced along the path, and ultimately to temporarily and passively anchor the distal end of the catheter in the desired position in the pulmonary artery.

When atrial fibrillation is detected, a defibrillating electrical shock in a range from about three to about seven joules is applied from external control and impulse generating equipment via an electrical connector at the catheter's proximal end and through electrical conductors to the electrodes, to establish an electric field with a vector through the right and left atria and having a sufficient gradient to reset the fibrillating cells and terminate the fibrillation. The patient is monitored continuously during high risk periods by the external control apparatus, to sense and instantaneously treat detected dysrhythmias.

According to the present invention, the control and impulse generating equipment (sometimes referred to herein as the control apparatus, control box, or control unit) to be located external to the patient's body for generating electrical shock impulses and other electrical treatment waveforms is electrically connected to the defibrillation electrodes of a flexible catheter, such as described in the '734 patent for example. The catheter is temporarily implanted in the patient's body with one defibrillation electrode positioned in the right atrium and the other elsewhere in the vicinity of the heart, preferably in the left pulmonary artery, to establish a vector through the atria for treatment of atrial fibrillation, for example. The control unit enables selective application of a shock impulse across the defibrillation electrodes with a magnitude to establish an adequate field gradient between the electrodes to cardiovert atrial fibrillation to normal sinus rhythm. The electrical shock impulse may be a biphasic pulse wave, with energy content adjustable within a range form about one to approximately 30 joules, and optimally between one and ten joules. The control unit cardiac rhythm for detection of the QRS complex of the ECG, to synchronously trigger delivery of a shock impulse therewith.

The monitoring equipment includes a display screen for displaying an atrial ECG signal derived from a sensing electrode of the catheter positioned in the right atrium and an intracardiac ECG signal derived from a sensing electrode of the catheter in the right ventricle, along with a surface ECG signal derived from surface electrodes in electrical contact with the patient's body. The monitoring portion of the control unit also includes a display screen indicator to display correct triggering of each shock impulse relative to the QRS complex, to avoid false triggering of a shock impulse. A strip chart recorder on the external control unit enables the recording of events before, during and after application of a shock impulse.

For treating other common detected arrhythmias, the control unit stimulus generator supplies stimulating pulses for application to the heart via pacing electrodes on the catheter.

BRIEF DESCRIPTION OF THE DRAWINGS

The above and still further aims, objects features, aspects, and attendant advantages of the invention will become apparent from the following description of the presently contemplated best mode of practicing the invention with reference to a presently preferred embodiment and method thereof, in conjunction with the accompanying drawings, in which.

DETAILED DESCRIPTION OF EMBODIMENTS AND METHODS OF THE INVENTION

Figure 1:
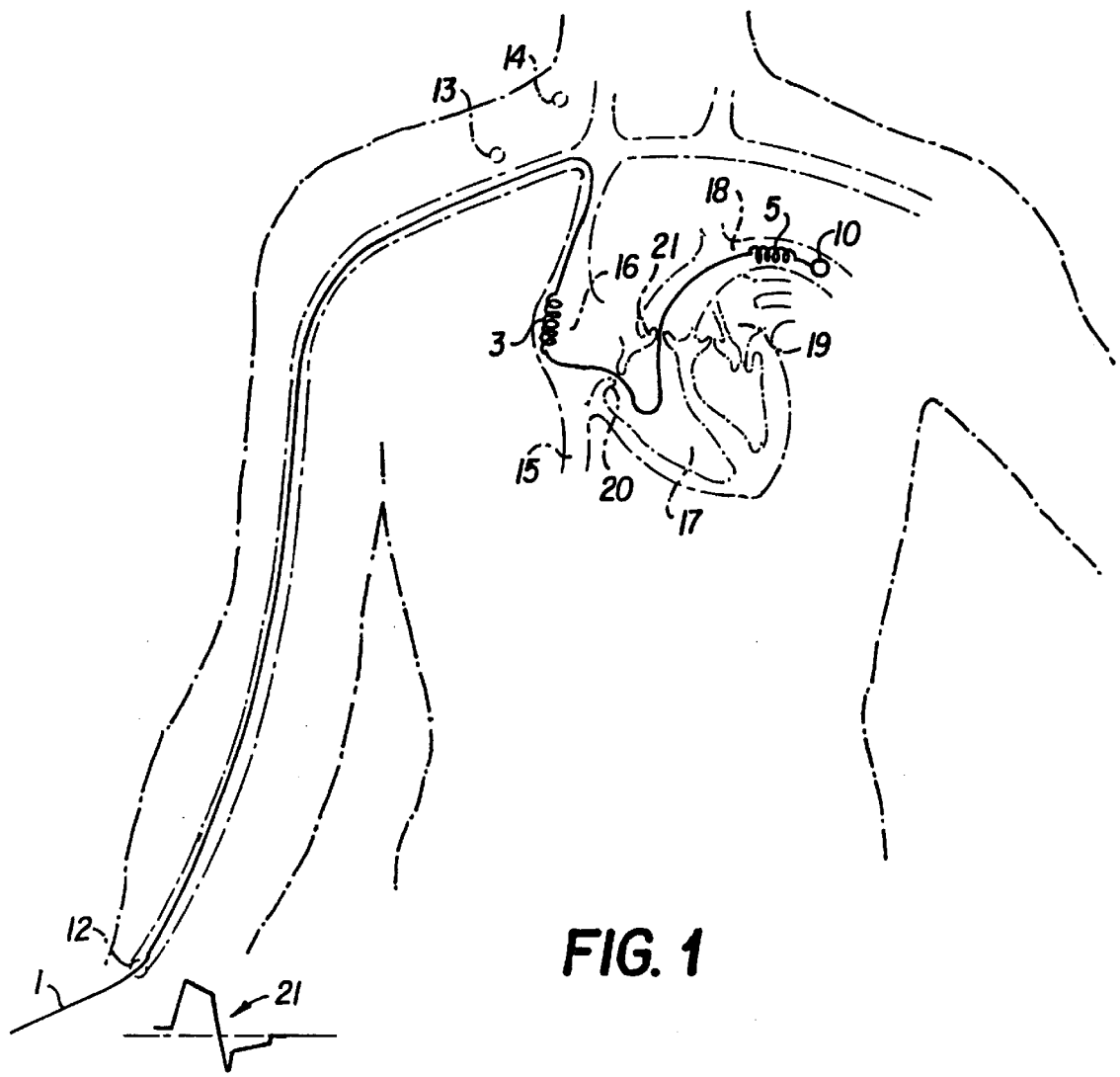
FIG. 1 is an illustration of placement of an atrial defibrillation catheter in the patient.

Referring to FIG. 1, a catheter 1 is inserted into the patient's body through a brachial vein puncture site 12 in the right arm and is advanced along the venous system to pass through the superior vena cava and into the right atrium 16 of the heart. The catheter is threaded through a path that includes the right atrium 16, the tricuspid valve 20, the right ventricle 17, the pulmonary valve 21, and finally into the left pulmonary artery 18 adjacent the left atrium 19. Internally embedded conductors 2 and 4 (FIGS. 2, 3) run substantially the length of the catheter from the proximal end where they terminate in connections to an external electrical connector 7 to the distal end where they terminate in electrical connections to defibrillation electrodes 3 and 5 (FIG. 2), respectively. Electrode 5 is located distally of electrode 3, i.e., closer to the distal tip of the catheter. When catheter 1 is fully threaded into position with its distal tip in the left pulmonary artery 18, defibrillation electrode 5 resides in the pulmonary artery and defibrillation electrode 3 resides in the right atrium.

The catheter typically has a diameter of about two millimeters (mm), and is constructed of a polymer sheath to give it sufficiently flexible to pass through the venous system and along the path to its final position shown in FIG. 1. Electrical conductors 2 and 4 are flexible stranded wires suitable for carrying sufficient current called for by the total energy (typically, on the order of three to seven joules) in the shock impulse generated by the external control unit 30 (FIG. 5) to electrodes 3 and 5 to achieve defibrillation. To that end, electrical connector 7 is connected via a mating connector (not shown) to the external control unit for monitoring and instantaneous treatment of atrial dysrhythmias.

Figure 2:
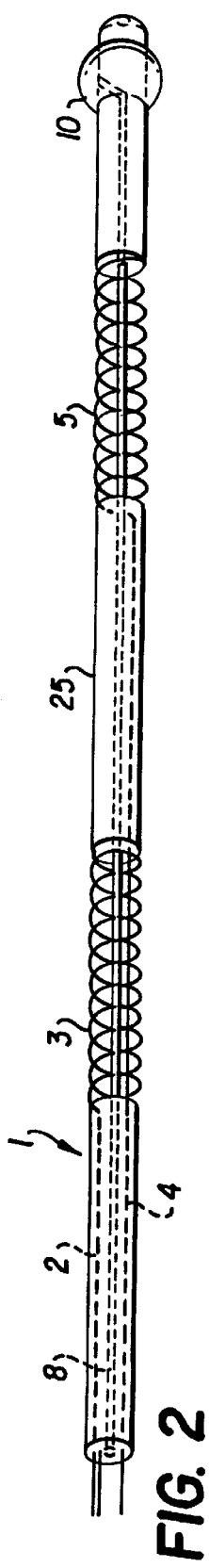
FIG. 2 is a perspective view, partly in section, principally of the distal portion of the catheter including the defibrillation electrodes.
Figure 3:
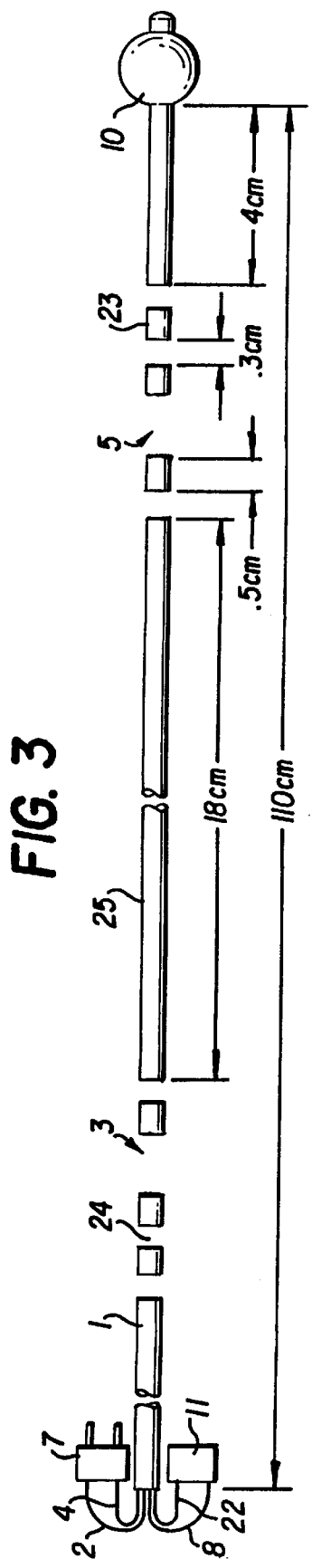
FIG. 3 is a partial side view of the catheter showing certain structural details.
Figure 4:
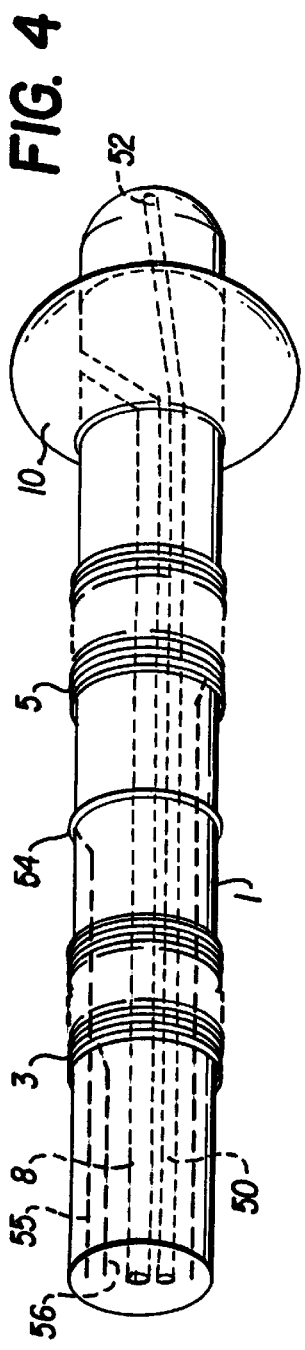
FIG. 4 is a partial perspective view of the distal portion showing some of its lumens.

The structure of electrodes 3 and 5 is critical for defibrillation, requiring a significant electrode surface exposure area to blood and tissue of the heart for transmitting the necessary shock impulse energy. Preferably, the shock impulse is a biphasic impulse, having a waveform 26 as shown in FIG. 1. To achieve the required surface area and locations for the defibrillation electrodes, they are constructed as shown in FIGS. 2, 3, and 4.

The overall length of catheter 1 is approximately 110 centimeters (cm) and, as previously noted, the outside diameter is typically about two mm. An inflatable balloon 10 is affixed to the distal tip of the catheter and is inflated and deflated through lumen 8 of the catheter which extends from the proximal end at a plug 11 (FIG. 3). The plug provides air control to the balloon by connection to an external syringe of two cc (not shown). Also, for monitoring the blood and the wedge pressure in or near the left pulmonary artery, and for taking blood samples and infusion of fluids to the body, which is particularly critical at the post-operative stage, a further lumen 22 is provided which terminates at or near the distal end of the catheter.

Each of electrodes 3 and 5 is constructed of a series of approximately 0.5 cm long rings 23, typically nine, separated by approximately 0.2 to 0.3 cm spacings 24. The distal electrode 5 is spaced about four cm from the balloon 10, and the two electrodes 3, 5 have an insulating sheath spacer 25 about eighteen cm long between them. The stainless steel rings 23 and interim spacings 24, which constitute insulating catheter sheath polymer material, provide a smooth surface which will not irritate human tissue when passed through the venous system. The area and length of the rings is sufficient to create an electric field gradient of adequate strength through the heart to reset substantially all atrially defibrillating cells and establish sinus rhythm with short duration shock impulse energy of an average of three joules, as confirmed by a study conducted by the applicant in patients with atrial fibrillation following an enlarged and diseased atrium.

The very flexible spacer sheath 25 between the electrodes requires only one electrical wire and is smooth and small diameter so that its position through the pulmonary artery valve 21 for reasonable periods of time will not adversely affect the function of that valve, or of the tricuspid valve 20 through which the catheter also extends. Thus, the catheter may be left in place for several days in a post-operative stage for monitoring and defibrillating in the event atrial fibrillation is detected. Also, the flexible sheath polymer spacers 24 between the stainless steel rings 23 afford enough flexibility at the electrode sites to bend the catheter about body cavities during insertion and positioning of the catheter in the heart. Other types of electrodes such as braided metal mesh would also serve for use as shocking electrodes 3 and 5.

In inserting the catheter, the balloon is initially partly inflated while in the right atrium so as to act as a sail and facilitate the positioning of the catheter by its being carried in the direction of the blood flow through the aforementioned path and into the pulmonary artery, for example. When the distal tip of the catheter reaches the final position in the left pulmonary artery, the balloon is fully inflated from the inflation lumen at the proximal end, to maintain the distal tip in stable position during its temporary placement for treatment. Fixation of the distal tip serves additionally to allow manipulating the shocking electrode 3 into contact with the atrium 16 for good electrical contact when the defibrillation pulse is applied, without danger that the catheter will be dislodged from the anchoring provided at the distal tip. Further, inflation and deflation of the balloon enables measurements of pulmonary wedge pressures.

Alternatively, the catheter may be inserted at the subclavian puncture site 13 or the internal jugular site 14. It would also be possible to approach through the femoral vein and the inferior vena cava 15. In any event, the critical positioning of the catheter and its electrodes shown in FIG. 1 permits a vector of electrical energy to pass through the left atrium 18.

Figure 5:
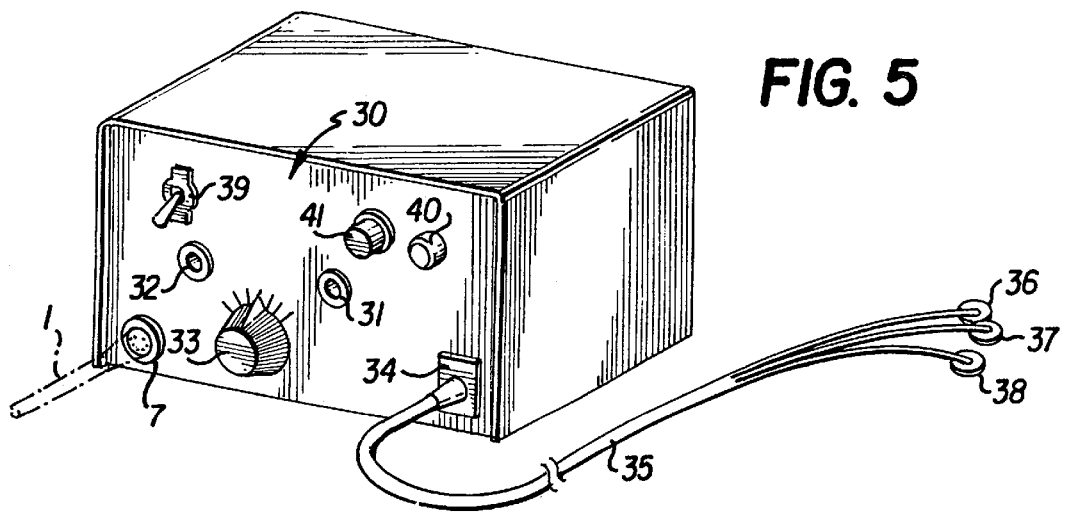
FIG. 5 is a perspective view of an external control apparatus of the invention.

The external atrial defibrillator 30 is the control unit shown in FIG. 5. It provides an electrical shock impulse, preferably biphasic (26, FIG. 1) of variable duration, preferably having a first phase pulse of four milliseconds (ms) duration, with a second phase pulse of opposite polarity to that of the first phase pulse and a duration of two and one half ms. The external defibrillator also provides variable energy by appropriate adjustment of knob 33 on the front panel of the defibrillator box, to deliver electrical energy in a range from about one to about 30 joules, preferably from one to 10 joules. Jacks 31 and 32 (or a single electrical connector 7) on the front panel of the box permit the anode and cathode leads 2, 4 of the catheter 1 to be connected to the defibrillator. ECG lead 35 with surface electrodes 36,37, 38 is used for triggering the defibrillation shock pulse synchronously with the R-wave or the QRS complex. The external defibrillator is turned on and off with switch 39. A temporary mode indicating correct synchronization with the R-wave, or the QRS complex, is indicated by a light-emitting diode (LED) 40 when the momentary switch 41 is depressed for testing without generating shock pulses. Other controls may include atrial fibrillation detectors that can be coupled to automatically generate a shock wave under prescribed conditions, and fluid controls for lumens 8 and 22 to monitor internal body fluids and provide for balloon inflation.

In the depiction of FIG. 4, lumen 50 extends through the catheter to an opening 52 at the distal tip for ingress and egress of blood and body fluids. An additional electrode ring 54 intermediate the defibrillation electrodes 3 and 5 is connected to electrical conductor wire 55 and is arranged on the catheter to be positioned in the right ventricle 17 when the temporary catheter is filly in position, for use in sensing intracardiac ECG activity and pacing the ventricle. Another electrode corresponding to ring 54 together with a separate conductor wire corresponding to 55 to which it is connected may be positioned closer to defibrillation electrode 3 so as to be located in the right atrium 16 when the catheter is fully implanted in the temporary configuration. The additional electrode is used for sensing atrial ECG activity and for pacing the atrial chamber. Preferably both of these sensing/pacing electrodes are arranged and located on the catheter so as to be maneuvered into contact with excitable tissue in the respective chamber. These electrodes together with the defibrillation electrodes may be used alternatively to or in addition to the surface electrodes 36, 37 and 38 to sense the R-wave and the QRS complex for triggering the delivery of a defibrillation shock impulse (biphasic pulse 26) in synchronization with the QRS complex. Proper initiation of the shock is important to avoid inducing ventricular fibrillation, which can occur as a consequence of non-synchronized application of the shock.

Figure 6:
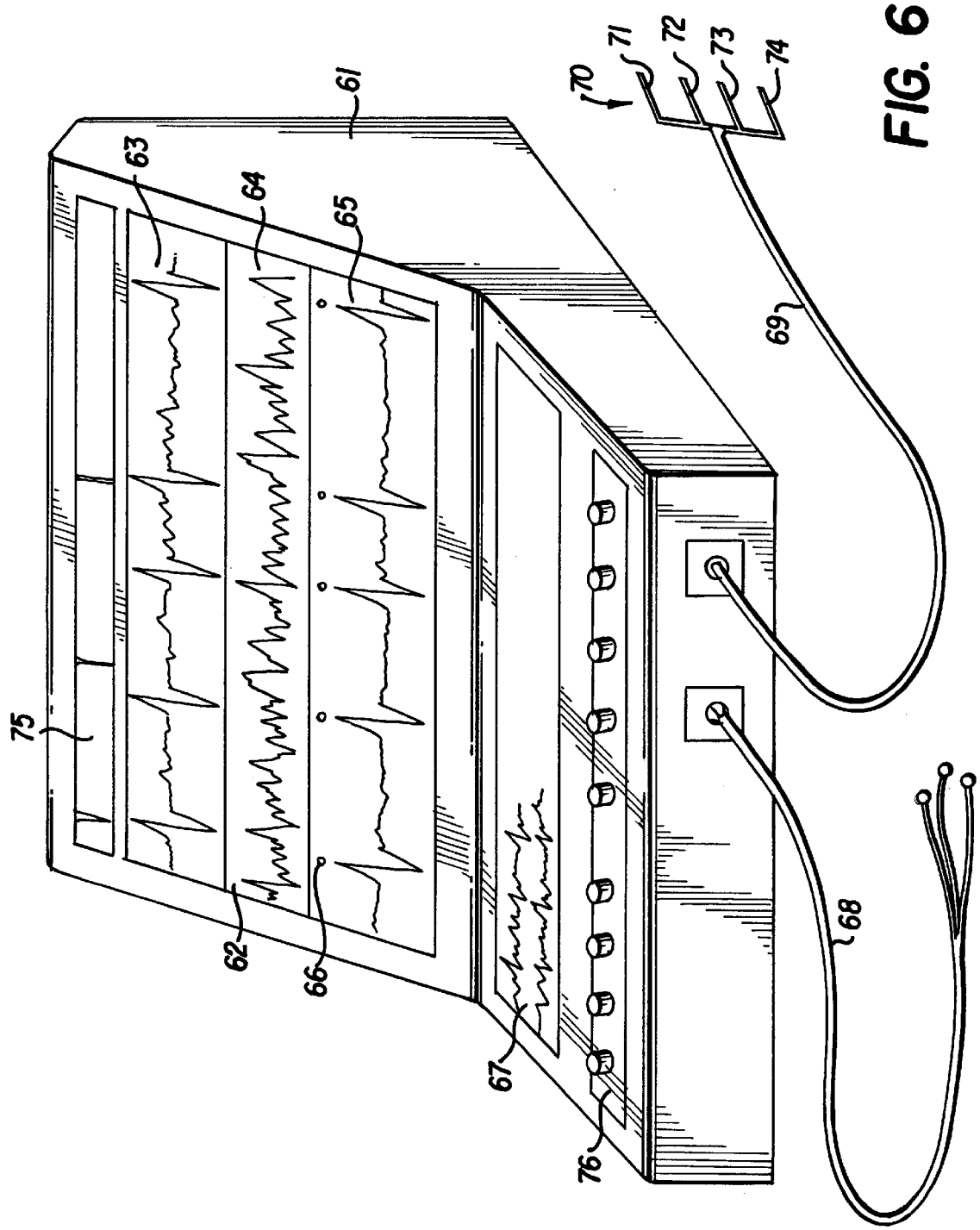
FIG. 6 is a perspective diagram of external monitoring and control apparatus of the invention.

Referring to FIG. 6, a preferred embodiment of the external atrial defibrillator includes a control unit 61 which includes a monitor, preferably a plasma display screen 62. The surface ECG signal 63 obtained from the surface electrodes when in place on the patient is monitored in one portion of the display, while additional signals representative of atrial activity 64 and the intracardiac ECG activity 65 are displayed on the screen as derived from the atrial and ventricular sensing/pacing electrodes respectively. The display signal 64 is indicative of atrial fibrillation, at the particular time that signal is presented on the screen 62. The triggering of the electrical shocks from the control unit 61 is indicated by dots 66 on the display screen, which indicate that the amplification (and sensitivity) is not too low to preclude reliable detection of the signals and not too high to cause false triggering (false shocking) to take place. Additionally, the control unit 61 has an ECG strip recorder to record on strip 67 the surface ECG signal derived from the surface electrodes of lead 68 when placed in contact with the patient's body. Lead 69 is a schematic representation of the atrial defibrillation catheter (or at leads symbolic of the electrical conductors therein), which is connected by means of an electrical connector to the control unit. Lead 69 has four plug type connections 70. Connection 71 is for the atrial defibrillation electrode (array) 3, connection 72 is for the atrial pacing ring, connection 73 is for the ventricular pacing ring, and connection 74 is for the distal defibrillation electrode 5. Shocks are applied between connections 71 and 74, and triggering is preferably accomplished between 72 and 73 (although other vectors may alternatively be used, if desired).

For tracing 74, the signals are from connections 71 and 72, and for the tracing 75 the signals from connection 73 is displayed relative to the connection 74 for the distal array. Automatic or manually adjustable gain control is used to aid in providing proper triggering, but as an alternative a triggering wire surface electrode of lead 68 may be used.

A control field 75 on the plasma screen operates in a "windows-like" environment, with appropriate knobs and switches on an operating panel 76 of the control unit serving to operate a cursor on the display 75 to enable selection of the appropriate energy sensing and pacing level, and as well for selection of the application of pacing pulses and the triggering of shocking pulses. Operating panel 76 may also be used to control the windows panel 75 for ECG leads, ECG amplification, and ECG control.

It will thus be seen that the present invention provides an external atrial defibrillator for use over limited periods of time to instantaneously treat dysrhythmias and fibrillation of a patient's heart by use of an external control box that generates electrical shocks of sufficient energy for cardioverting atrial fibrillation, as well as stimulating pulses for pacing the patient's heart when required. The control box is electrically connected to the lead which is temporarily inserted in the patient's heart, for delivering the electrical shocks through the atria for the cardioversion. The control unit shock impulse generator is triggered to selectively initiate application of the electrical shocks to the heart lead in synchronism with a designated portion of the patient's ECG, specifically, the QRS complex.

Although certain presently preferred embodiments and methods of treatment have been described herein, various modifications of the invention will become apparent to persons of ordinary skill in the field from a consideration of the foregoing detailed description, without departing from the spirit and scope of the invention. It is therefore desired that the present invention shall be limited only by the appended claims and by the rules and principles of applicable law.

What is claimed is:

1. A method for external treatment of dysrhythmias including fibrillation of a patient's heart, comprising the steps of providing a control box for generating electrical waveforms including shocks of variable energy content sufficient for terminating said dysrhythmias; inserting a lead having transvenous defibrillation electrodes through a portion of the patient's venous system to position said electrodes to produce an electric field vector through the patient's heart when an electrical shock of sufficient energy content is applied across said electrodes; electrically connecting said control box to said lead to deliver electrical shocks generated by said control box to said defibrillation electrodes, and to deliver a representation of the patient's ECG waveform to said control box; synchronously triggering the generation of said electrical shocks from said control box in response to detection of a preselected portion of said ECG waveform; and adjusting the energy content of each of said electrical shocks to a value within a range from one to thirty joules to terminate a detected event of fibrillation.

2. The method of claim 1, wherein said preselected portion of said ECG waveform is a QRS complex.

3. The method of claim 2, including displaying correct triggering of each of said electrical shocks relative to the QRS complex of said ECG waveform on a display screen of said control box to avoid improper triggerings.

4. The method of claim 1, including passively anchoring said lead in place when said defibrillation electrodes are in desired position by inflating a balloon at the distal end of said lead through an inflation lumen thereof.

5. The method of claim 1, wherein said detected event of fibrillation is atrial fibrillation.

6. Apparatus for external treatment of dysrhythmias including fibrillation of a patient's heart, comprising a control box adapted to be located externally of a patient's body for generating electrical waveforms including shocks of variable energy content sufficient for terminating said dysrhythmias; a lead having transvenous defibrillation electrodes adapted for insertion through a portion of the patient's venous system to position said electrodes to produce an electric field vector through the patient's heart when an electrical shock of sufficient energy content is applied across said electrodes from said control box; said control box electrically connected to said lead to deliver electrical shocks to said defibrillation electrodes, and to portray a representation of the patient's ECG waveform; means in said control box for synchronously triggering the generation of said electrical shocks therefrom in response to detection of a preselected portion of said ECG waveform; and means in said control box for adjusting the energy content of each of said electrical shocks to a value within a range from one to thirty joules to terminate a detected event of fibrillation.

7. The apparatus of claim 6, wherein said preselected portion of said ECG waveform is a QRS complex.

8. The apparatus of claim 7, wherein said control box includes a screen for displaying correct triggering of each of said electrical shocks relative to the QRS complex of said ECG waveform to avoid improper triggerings.

9. The apparatus of claim 6, including a balloon located at the distal end of said lead for passively anchoring said lead in place when said defibrillation electrodes are in desired position by inflating said balloon through an inflation lumen of the lead.

* * * * *